United States Patent
Fukumoto et al.

(10) Patent No.: US 8,507,626 B2
(45) Date of Patent: Aug. 13, 2013

(54) CATALYST FOR PRODUCING OF ACRYLIC ACID, METHOD FOR PRODUCING ACRYLIC ACID USING THE CATALYST AND METHOD FOR PRODUCING WATER-ABSORBENT RESIN USING THE ACRYLIC ACID

(75) Inventors: Naohiro Fukumoto, Aioi (JP); Toshiya Nishiguchi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 123 days.

(21) Appl. No.: 12/452,013

(22) PCT Filed: May 28, 2008

(86) PCT No.: PCT/JP2008/060242
§ 371 (c)(1),
(2), (4) Date: Dec. 11, 2009

(87) PCT Pub. No.: WO2008/152952
PCT Pub. Date: Dec. 18, 2008

(65) Prior Publication Data
US 2010/0121007 A1 May 13, 2010

(30) Foreign Application Priority Data

Jun. 13, 2007 (JP) ................................. 2007-156042

(51) Int. Cl.
*C08F 20/06* (2006.01)
*C08F 4/22* (2006.01)
*B01J 23/22* (2006.01)
*B01J 21/06* (2006.01)
*B01J 23/28* (2006.01)
*C07C 51/235* (2006.01)
*C07C 51/215* (2006.01)

(52) U.S. Cl.
USPC ........ 526/317.1; 526/113; 502/312; 502/248; 502/309; 502/310; 562/535; 562/549

(58) Field of Classification Search
USPC .............. 526/113, 317.1; 502/312, 248, 309, 502/310; 562/535, 549
See application file for complete search history.

(56) References Cited

U.S. PATENT DOCUMENTS

| 4,891,347 A | 1/1990 | Oh-Kita et al. | |
|---|---|---|---|
| 4,892,856 A * | 1/1990 | Kawajiri et al. | 502/247 |
| 5,380,933 A | 1/1995 | Ushikubo et al. | |
| 5,739,392 A | 4/1998 | Tanimoto et al. | |
| 6,174,978 B1 * | 1/2001 | Hatsuda et al. | 526/240 |
| 7,217,680 B2 | 5/2007 | Teshigahara et al. | |
| 2004/0082810 A1 * | 4/2004 | Borgmeier et al. | 562/546 |

FOREIGN PATENT DOCUMENTS

| EP | 0 608 838 | 8/1994 |
|---|---|---|
| EP | 608838 A2 * | 8/1994 |
| EP | 1 375 466 | 1/2004 |
| EP | 1375466 A1 * | 1/2004 |
| EP | 1 574 254 | 9/2005 |
| JP | 2003-220337 | 8/2003 |

OTHER PUBLICATIONS

International Search Report issued Oct. 17, 2008 in International (PCT) Application No. PCT/JP2008/060242.
PCT Written Opinion issued Oct. 17, 2008 in International (PCT) Application No. PCT/JP2008/060242.

* cited by examiner

*Primary Examiner* — Michael M Bernshteyn
(74) *Attorney, Agent, or Firm* — Wenderoth, Lind & Ponack, L.L.P.

(57) ABSTRACT

The invention provides a catalyst for producing acrylic acid at high yield for a long time, in a method for producing acrylic acid by catalytic gas phase oxidation of propane and/or acrolein in the presence of molecular oxygen or a molecular oxygen-containing gas. This catalyst comprises a complex oxide containing molybdenum, vanadium and X component (here the X component is at least one element selected from antimony, niobium and tin) as the essential components, and is characterized in that its main peak as measured by X-ray diffractiometry using $K\alpha$ ray of Cu, $d=4.00\pm0.1$ angstrom, and in that the particle size of the X component in the catalyst does not exceed 20 μm.

8 Claims, No Drawings

CATALYST FOR PRODUCING OF ACRYLIC ACID, METHOD FOR PRODUCING ACRYLIC ACID USING THE CATALYST AND METHOD FOR PRODUCING WATER-ABSORBENT RESIN USING THE ACRYLIC ACID

TECHNICAL FIELD

This invention relates to catalysts for producing acrylic acid by catalytic gas phase oxidation of propane and/or acrolein in the presence of molecular oxygen or molecular oxygen-containing gas, method for producing acrylic acid using the catalyst, and also to method for producing water-absorbent resin using the acrylic acid.

Acrylic acid is industrially important as a starting material for various synthetic resins, paint and plasticizing agent. The importance is still increasing in recent years, particularly as a starting material for water-absorbent resins. As the method for producing acrylic acid, the most commonly practiced is the two-stage oxidation method comprising producing acrolein by catalytic gas phase oxidation of propylene and then obtaining acrylic acid by catalytic gas phase oxidation of the acrolein.

Whereas, because of the difference in price between propane and propylene, development of single stage oxidation of propane to produce acrylic acid is recently under progress, and various proposals have been made thereabout.

As catalyst for producing acrylic acid by catalytic gas phase oxidation of propane and/or acrolein in the presence of molecular oxygen or molecular oxygen-containing gas, molybdenum-vanadium catalyst has been at the center of investigation, with which however satisfactory catalytic performance such as the object acrylic acid yield or the catalyst life is not necessarily obtained, and various proposals have also been made to improve the catalytic performance.

For instance, proposals concerning acrylic acid producing method by catalytic gas phase oxidation of acrolein include the following: JP Hei 8 (1996)-206504A (=U.S. Pat. No. 5,739,392) disclosed use of specific compounds as the supply sources of vanadium, copper, antimony and tin; use of antimony oxide in which the antimony has a valency more than 0 but less than 5 as at least a part of the antimony supply source; and use of tin oxide in which the tin has a valency more than 0 but less than 4 as at least a part of the tin supply source. JP 2005-329363A (=U.S. Pat. No. 7,217,680B2) disclosed use of isometric system antimony trioxide as at least a part of the antimony-supply source compound. JP 2003-220337A disclosed use as the antimony supply source a heat-treated silicon carbide-containing complex oxide represented by a formula Sb—Ni—X—SiC—O (X being selected from Si and Al); and use as the niobium-supply source niobium ammonium oxalate compound. JP Sho 61 (1986)-114739A (=U.S. Pat. No. 4,891,347) disclosed that a complex oxide comprising phosphorus, molybdenum and antimony, which was prepared using antimony trioxide of an average particle size not greater than 0.2 μm, was useful as the catalyst for producing unsaturated carboxylic acid by gas phase oxidation of unsaturated aldehyde.

Problem to be Solved by the Invention

Acrylic acid is currently manufactured at a scale of several million tons per year and, hence, an improvement in the industrial scale yield even by 0.1% would bring about substantial economical merit. Above-described catalysts, however, leave room for further improvement at an industrial scale, although they all achieved the intended improvements in catalytic performance such as acrylic acid yield or catalyst life.

Afore-cited method of JP Hei 8 (1996)-206504A (=U.S. Pat. No. 5,739,392) accomplishes relatively high catalytic performance such as acrylic acid yield and life, but requires the use of special compounds as the supply sources of catalytic ingredients and hence leaves problems in stable starting material supply or reproducibility, for industrial scale catalyst preparation.

It is true that the methods of above JP 2005-329363A (=U.S. Pat. No. 7,217,680B2) and 2003-220337A achieved very high acrylic acid yields, but they were obtained in small scale experiments under largely different conditions from those for industrial scale production. For example, the acrylic acid yield disclosed in the former was that obtained in laboratory level small scale experiments conducted by filling a reaction tube of 4 mm in inner diameter with 0.3 g of the catalyst which had been pulverized to 20-28 mesh and dressed.

Also the catalyst of the cited JP Sho 61 (1986)-114739A (=U.S. Pat. No. 4,891,347) contains phosphrous, molybdenum and antimony as the essential components, and has a Keggin type heteropolyacid structure as seen from their composition ratios as given in working examples. The catalyst is effective for methacrylic acid production through oxidation of methacrolein, but its effectiveness in industrial scale acrylic acid production by oxidation of acrolein is questionable. In fact, the acrylic acid yield level shown in its Examples is unsatisfactory.

Thus, an object of the present invention is to provide a catalyst for producing acrylic acid on industrial scale stably at high yield for a long time, by catalytic gas phase oxidation of propane and/or acrolein in the presence of molecular oxygen or a molecular oxygen-containing gas.

Another object of the invention is to provide a method for producing acrylic acid by catalytic gas phase oxidation of propane and/or acrolein in the presence of molecular oxygen or a molecular oxygen-containing gas, using such a catalyst.

Still other object of the present invention is to provide a method for producing water-absorbent resin, using such acrylic acid.

Means for Solving the Problems

We have engaged in concentrative studies aiming at solving the above problems, to now discover that they could be easily solved by using as the catalyst a complex oxide containing molybdenum, vanadium and X component (here the X component is at least one element selected from antimony, niobium and tin) as the essential components, in which the main peak d=4.00±0.1 Å as measured with X-ray diffractiometry using Kα ray of Cu, and the X component particles in the catalyst have a size not exceeding 20 μm. The reason for the catalytic effect of this complex oxide is not necessarily clear, but presumably the finely dispersed X component particles in the catalyst containing the oxide of specific crystalline structure increase the active points exhibiting the catalytic activity, and furthermore the maintenance of their finely dispersed state during the use for a long time has an effect to suppress aggregation of other components and sustain the active points.

Effect of the Invention

In consequence of thus solving the problems, the invention can provide a catalyst for producing acrylic acid at high yield stably for a long time by catalytic gas phase oxidation of propane and/or acrolein in the presence of molecular oxygen or a molecular oxygen-containing gas; and can produce acrylic acid at high yield for a long time, using that catalyst.

BEST MODE FOR CARRYING OUT THE INVENTION

Hereinafter the catalyst for producing acrylic acid and method for producing acrylic acid using the same catalyst of the invention are explained in details, it being understood that the invention is not restricted by the explanation but can be worked with suitable alteration within a scope not impairing the purpose of the invention.

The catalyst used in the invention contains molybdenum, vanadium and X component as the essential components. In particular, it is a catalyst for producing acrylic acid containing a complex oxide represented by the following general formula (1):

$$Mo_a V_b X_c A_d B_e C_f D_g O_y \qquad (1)$$

(wherein Mo is molybdenum; V is vanadium; X is at least one element selected from antimony, niobium and tin; A is at least one element selected from tungsten, nickel, cobalt, tellurium and bismuth; B is at least one element selected from iron, copper, lead and zinc; C is at least one element selected from silicon, titanium and zirconium; D is at least one element selected from alkali metals; and O is oxygen; and a, b, c, d, e, f, g and y are respective atomic ratios of Mo, V, X, A, B, C, D and O; where a=12, 1≦b≦15, 0.01≦c≦10, 0.02≦d≦6, 0.01≦e≦6, 0≦f≦60 and 0≦g≦10; and y is a numerical value determined by the state of oxidation of respective elements), which is characterized in that its main peak d=4.00±0.1 Å (angstrom) as measured by X-ray diffractiometry using Kα ray of Cu and that the size of the X component particles in the catalyst does not exceed 20 μm.

The catalyst of the present invention can be prepared by those methods commonly used for preparing this kind of catalysts, an example of which is as follows.

Starting materials of the catalytic components excepting X component are subject to no particular limitation, and commonly used ammonium salt, nitrate, carbonate, sulfate, hydroxide and oxide of each of the metal elements can be used. Also those complex oxides including the above composition may be used as starting materials.

As starting material of X component, insoluble compound(s) having an average particle size not more than 100 nm, preferably not more than 50 nm, inter alia, not more than 20 nm, can be advantageously used for rendering the size of the X component in the catalyst not more than 20 μm. In particular, oxide(s) of the specified size can be conveniently used. Here the average particle size of X component is the average value of diameters of plural particles as measured with electron microscope or the like. As starting materials of X component, commercial products having such particle diameters can be used as they are, or as pulverized to above-specified particle size. Water-soluble compound (e.g., antimony tartrate) is unsuitable as a starting material of X component, because it dissolves and is apt to induce unnecessary reaction with other components at the preparation stage of the catalyst, and furthermore is extremely easy to aggregate in drying step or the like.

Those starting materials are formed into a starting liquid mixture by such means as dissolving or suspending them in solvent such as water. In that occasion, the starting materials may be successively mixed into water, or they may be formulated into plural starting liquids according to their kinds and which liquids are successively mixed. There is no particular limitation to the mixing conditions (order of mixing, temperature, pressure, pH, etc.) Normally the reaction among the starting materials progresses at this stage, and in occasions particles in the liquid mixture grow with the advance in the reaction. For reducing the particle size of X component in the catalyst, preferably fine division of the particles is carried out at this stage. For example, it is satisfactory to allow the reaction to progress, while pulverizing them with a pulverizer like a ball mill. The time to be consumed for the pulverization or reaction and the treating conditions should be suitably selected according to the kind and characteristics of individual apparatus used for the pulverization treatment and cannot be unconditionally specified, while the treatment can be given for 2-24 hours.

The resulting liquid mixture of the starting materials is dried by various means such as heating or pressure reduction, in order to prepare catalyst precursor. More specifically, for example, a powdery catalyst precursor may be formed with spray dryer, drum dryer or the like, or that in the form of blocks or flakes may be formed by heating in a gaseous current using a box-type dryer or tunnel type dryer or the like. The liquid mixture of starting materials may also be evaporated to dryness (concentration to dryness) to form solid cakes which then is heat-treated as above. As a means utilizing pressure reduction, for example, a vacuum dryer may also be used to make block- or powder-formed catalyst precursor.

Thus obtained dry catalyst precursor is optionally put through a pulverization step or classification step to provide a powder of appropriate particle size, and sent to the subsequent molding step. It also may be once calcined before being sent to the molding step. While particle size of the catalyst precursor is not particularly limited, it is preferably not more than 500 μm, for excellent moldability.

At the molding step, the catalyst precursor powder is molded into a fixed shape by well known extrusion molding process or tabletting molding process, or supported on optional inert carrier having a fixed shape, by such well known means as tumbling granulation method or rocking mixer method. As the means for supporting besides the above, the liquid mixture of starting materials may be left undried as it is or, where necessary, after being given a pulverization treatment, and absorbed by, or applied onto, a desired carrier to have the catalytic component supported on the carrier.

Where moldings are formed by extrusion process or tabletting process, their shape of course is not limited, which may be any of spherical, cylindrical, ring-formed or indeterminate. Where they are spherical, needless to say they are not necessarily true spheres. It is sufficient that they are substantially spherical, which applies also to cylindrical forms and ring-like forms.

When a supporting method is adopted, generally known inert carriers such as alumina, silica, silica-alumina, titania, magnesia, steatite, silica-magnesia, silicon carbide, silicon nitride, zeolite and the like can be used as the inert carrier. Shape of the carrier is again subject to no particular limitation, but it can be of any known shape such as spherical, cylindrical, ring-formed or the like.

In the above molding step, at the time of molding the catalyst precursor powder, various substances used for various purposes in catalyst preparation in general, such as molding aid or binder for improving moldability, pore-forming agent for forming adequate pores in the catalyst, and the like can be used. Specific examples include ethylene glycol, glycerine, propionic acid, maleic acid, benzyl alcohol, propyl alcohol, butyl alcohol, phenols, water, nitric acid, ammonium nitrate, ammonium carbonate and the like. Also for the purpose of improving mechanical strength of the catalyst, reinforcing agent may be used. Specific examples include graphite, glass fiber, silicon carbide, silicon nitride and the like, which are generally known as reinforcing agent. Such reinforcing agent may be added halfway the preparation step of the catalyst precursor, or may be blended with the prepared catalyst precursor. Furthermore, for regulating activity of the catalyst, powder of inert substance not participating in the reaction may also be used, specific examples including alumina and molybdenum trioxide. Such inert substance powder may be added halfway the catalyst precursor preparation, or it may be blended with the prepared catalyst precursor.

The catalyst of the present invention may be a molded catalyst in which the catalytic components are molded into a fixed shape, a supported catalyst in which the catalytic components are supported on an optional inert carrier of a fixed shape, or may be a combination of these molded catalyst and supported catalyst.

The molded or supported catalyst as obtained in the above molding step is then sent to a calcining step. The calcining temperature preferably ranges 350° C.-450° C., in particular, 380° C.-420° C. The calcining time preferably ranges 1-10 hours. The calcining oven is subject to no particular limitation. Commonly used box-type calcining oven or tunnel-type calcining oven or the like may be used.

The reactor to be used in the present invention for producing acrylic acid by catalytic gas phase oxidation of propane and/or acrolein in the presence of molecular oxygen or a molecular oxygen-containing gas is subject to no particular limitation. For example, any of fixed bed reactor, fluidized bed reactor, moving bed reactor and the like can be used, while normally a fixed bed reactor is used.

The reaction conditions again are subject to no particular limitation, and the reaction can be carried out under any conditions heretofore generally used for this kind of reaction. For example, a reaction gas composed of 1-15 volume %, preferably 4-12 volume % of propane and/or acrolein, 0.5-25 volume %, preferably 2-20 volume % of molecular oxygen, 0-30 volume %, preferably 0-25 volume % of steam and the balance of an inert gas such as nitrogen, is contacted with the oxidation catalyst at temperatures ranging 200-400° C. under pressures ranging 0.1-1.0 MPa, and at space velocities ranging 300-5,000 h$^{-1}$ (STP).

As the reaction gas, not only gaseous mixtures composed of propane and/or acrolein, oxygen and inert gas as above, but gaseous mixtures containing acrolein which are obtained through dehydration reaction of glycerine or oxidation reaction of propylene can be used, to which air or oxygen may be added where necessary.

The acrylic acid-containing gas obtained by such catalytic gas phase oxidation as above-described is collected as acrylic acid-containing liquid by the means known per se, such as absorption into solvent, e.g., water or high boiling point hydrophobic organic matter, or direct condensation. Upon purification of the acrylic acid-containing liquid by known means such as extraction, distillation or crystallization, purified acrylic acid is obtained.

Thus obtained purified acrylic acid (and/or a salt thereof) or a monomeric mixture containing the same as the chief component (preferably at least 70 mol %, in particular, at least 90 mol %) is crosslinking polymerized using about 0.001-5 mol % (to the acrylic acid) of a crosslinking agent and about 0.001-2 mol % (to the acrylic acid) of a radical polymerization initiator. The formed polymer is dried and pulverized to provide a water-absorbent resin.

"Water-absorbent resin" refers to water-swellable and water-insoluble polyacrylic acid having crosslinked structure, which absorbs at least 3 times, preferably 10-1,000 times, its own weight of pure water or physiological saline solution to form water-insoluble hydrogel preferably containing no more than 25 mass %, in particular no more than 10 mass %, of water-soluble component. Examples of such water-absorbent resin or their physical property-measuring methods are described, for example, in U.S. Pat. Nos. 6,107,358, 6,174,978 and 6,241,928.

EXAMPLES

Hereinafter the present invention is explained still more specifically, referring to Examples, but the invention is in no way restricted thereby. Furthermore, "mass part" may be hereafter written simply as "part", for convenience. Acrolein conversion and acrylic acid yield given in the Examples are defined as follows:

$$\text{acrolein conversion (mol \%)} = \frac{\text{(number of mols of reacted acrolein)}}{\text{(number of mols of supplied acrolein)}} \times 100$$

$$\text{acrylic acid yield (mol \%)} = \frac{\text{(number of mols of formed acrylic acid)}}{\text{(number of mols of supplied acrolein)}} \times 100$$

[Measurement of Particle Size of X Component in the Catalyst]

EPMA-1610 manufactured by Shimadzu Corporation was used to measure the size of the X component particles in the catalyst. Specifically, distribution state of the X component particles in each 256 µm square of the surface and cross-section of each catalyst were mapped and the sizes of the particles were measured.

[X-Ray Diffraction of Catalyst]

X' Pert Pro MPD manufactured by Spectris Co., Ltd. was used, with Kα ray of Cu.

[Pulverization of Starting X Component Material]

As the X component used as a starting material, commercially available oxides were pulverized with Wet System Crusher Ready Mill RMB-08 Model manufactured by Aimex Co., Ltd.

[Measurement of Particle Size of Starting X Component Material]

Average particle size of X component was measured by electron micrograph method with ELECTRON MICROSCOPE JEM-100SX manufactured by JEOL Co., Ltd.

Example 1

Into 2500 parts of water under heating and stirring, 350 parts of ammonium paramolybdate, 97 parts of ammonium metavanadate and 93.5 parts of ammonium paratungstate were dissolved. Separately, 79.8 parts of copper nitrate was dissolved in 200 parts of water under heating and stirring. The resulting two aqueous solutions were mixed, and into the liquid mixture 24.1 parts of antimony trioxide whose average particle size had been made 20 nm by pulverization with Ready Mill was added to provide a liquid starting material mixture. This liquid starting material mixture was placed in a ball mill, pulverized and reacted for about 3 hours, and then evaporated to dryness to provide a solid cake. The cake was calcined at 390° C. for about 5 hours. The calcined solid was pulverized to a size not more than 250 μm to provide a catalyst powder. Into a centrifugal fluidized coating apparatus 1200 parts of spherical α-alumina carrier having an average particle size of 4.5 mm was thrown, followed by throwing supply of the catalyst powder together with 15 wt % of aqueous ammonium nitrate solution as a binder, through 90° C. hot air current to be supported on the carrier. Further heat-treating the supported catalyst at 400° C. for 6 hours in the atmosphere of air, a complex oxide catalyst was obtained. X-ray diffractiometry of this complex oxide catalyst found its main peak d=4.00. The supported ratio of this complex oxide catalyst was about 33%, and its composition was as follows. The size of the antimony particles in the catalyst was 2.6 μm.

$$Mo_{12}V_5Sb_1W_{1.2}Cu_2$$

Four-hundred (400) ml of the complex oxide catalyst as obtained was filled in a stainless steel U-formed tube having an inner diameter of 25 mm and into which a gaseous mixture composed of 4.0 volume % of acrolein, 22.5 volume % of air, 25 volume % of steam and the balance of inert gas such as nitrogen was introduced. The reaction was carried at a space velocity to the complex oxide catalyst of 1500 hr$^{-1}$. The reaction was continued for 4000 hours, and the catalyst performance at the initial reaction stage (24 hours after starting the reaction) and after 4000 hours of the reaction were examined. The result was as shown in Table 1.

Examples 2 and 3

A catalyst was prepared in the same manner to Example 1, except that the antimony trioxide of average particle size 20 nm as used as a starting material was replaced with 22.3 parts of stannous oxide (Example 2) or 22 parts of niobium pentoxide (Example 3), which had been each pulverized to an average primary particle size of 20 nm. Compositions of the metal components excepting oxygen of the resulting catalysts were respectively as follows:

$$Mo_{12}V_5Sn_1W_{1.2}Cu_2$$

$$Mo_{12}V_5Nb_1W_{1.2}Cu_2.$$

The main peaks in X-ray diffractiometry of these complex oxide catalysts were both d=4.00, and sizes of the tin particles and niobium particles in the catalysts were 7.2 μm and 6.6 μm, respectively.

Using these catalysts, oxidation reaction of acrolein was carried out in the same manner with Example 1. The results were as shown in Table 1.

Example 4

A catalyst was prepared in the same manner with Example 1, except that the liquid starting material mixture was not pulverized and reacted in the ball mill but was simply stirred. The resulting complex oxide catalyst had a main peak in X-ray diffractiometry of d=3.99. The size of the antimony particles in the catalyst was 13.4 μm. Using this catalyst, oxidation reaction of acrolein was carried out in the same manner with Example 1. The result was as shown in Table 1.

Example 5

A catalyst was prepared in the same manner with Example 4, except that antimony trioxide which had been pulverized with Ready Mill to an average particle size of 100 nm was used as a starting material. The resulting complex oxide catalyst had a main peak in X-ray diffractiometry of d=4.00. The size of the antimony particles in the catalyst was 19.3 μm. Using this catalyst, oxidation reaction of acrolein was carried out in the same manner with Example 1. The result was as shown in Table 1.

Example 6

A catalyst was prepared in the same manner with Example 1, except that antimony trioxide which had been pulverized with Ready Mill to an average particle diameter of 100 nm was used as a starting material. The resulting complex oxide catalyst had a main peak in X-ray diffractiometry of d=3.99. The size of the antimony particles in the catalyst was 14.5 μm. Using this catalyst, oxidation reaction of acrolein was carried out in the same manner with Example 1. The result was as shown in Table 1.

Comparative Example 1

A catalyst was prepared by the method as described in Example 2 of JP 61 (1986)-114739 (=U.S. Pat. No. 4,891,347), which was compression molded into pellets of 6 mm in outer diameter and 6 mm in length. Antimony trioxide which had been pulverized with Ready Mill to an average primary particle size of 20 nm similarly to Example 1 was used. The composition of the metal components of the catalyst excepting oxygen was as follows:

$$P_{1.5}Mo_{12}V_{0.5}Cu_{0.5}Ge_{0.5}K_1Sb_{0.8}.$$

When X-ray diffraction of this complex oxide catalyst was measured, its main peak d=3.42. The catalyst had a Keggin type heteropolyacid structure. The antimony particles in the catalyst had a size of 16.2 μm Using this catalyst, oxidation reaction of acrolein was carried out in the same manner with Example 1. The result was as shown in Table 1.

Comparative Example 2

A catalyst was prepared in the same manner with Example 1, except that antimony trioxide which had been pulverized with Ready Mill to an average particle size of 200 nm was used as a starting material. The resulting complex oxide catalyst had a main peak in X-ray diffractiometry of d=4.00. The size of the antimony particles in the catalyst was 24.2 μm. Using this catalyst, oxidation reaction of acrolein was carried out in the same manner with Example 1. The result was as shown in Table 1.

Comparative Example 3

A catalyst was prepared in the same manner with Example 4, except that antimony trioxide which had been pulverized with Ready Mill to an average particle size of 200 nm was used as a starting material. The resulting complex oxide catalyst had a main peak in X-ray diffractiometry of d=4.01. The size of the antimony particles in the catalyst was 35.6 μm. Using this catalyst, oxidation reaction of acrolein was carried out in the same manner with Example 1. The result was as shown in Table 1.

Comparative Example 4

A catalyst was prepared in the same manner with Example 1, except that the antimony trioxide was replaced with 55.2 parts of soluble antimonylpotassium tartarate. The composition of the metal components excepting oxygen was as follows:

$$Mo_{12}V_5Sb_1W_{1.2}Cu_2K_1.$$

The resulting complex oxide catalyst had a main peak in X-ray diffractiometry of d=4.00. The size of the antimony particles in the catalyst was 45.8 μm. Using this catalyst, oxidation reaction of acrolein was carried out in the same manner with Example 1. The result was as shown in Table 1.

TABLE 1

| | X component | Size of X component starting material (nm) | Size of X component in the catalyst (μm) | Pulverization of liquid starting material mixture | XRD main peak (Å) | Reaction time (Hr) | Reaction temp. (°C.) | Acrolein conversion (mol %) | Selectivity (mol %) | Single-pass yield of acrylic acid (mol %) |
|---|---|---|---|---|---|---|---|---|---|---|
| Example 1 | antimony-trioxide | 20 | 2.6 | yes | 4.00 | initial stage | 248 | 98.7 | 95.8 | 94.6 |
| | | | | | | 4000 | 250 | 98.8 | 95.7 | 94.6 |
| Example 2 | stannous oxide | 20 | 7.2 | yes | 4.00 | initial stage | 248 | 98.2 | 95.1 | 93.4 |
| | | | | | | 4000 | 251 | 98.1 | 94.9 | 93.1 |
| Example 3 | niobium pentoxide | 20 | 6.6 | yes | 4.00 | initial stage | 248 | 98.6 | 95.0 | 93.7 |
| | | | | | | 4000 | 252 | 98.6 | 95.0 | 93.7 |
| Example 4 | antimony-trioxide | 20 | 13.4 | no | 3.99 | initial stage | 250 | 98.5 | 94.9 | 93.5 |
| | | | | | | 4000 | 253 | 98.4 | 94.9 | 93.4 |
| Example 5 | antimony-trioxide | 100 | 19.3 | no | 4.00 | initial stage | 251 | 98.0 | 94.7 | 92.8 |
| | | | | | | 4000 | 255 | 97.6 | 94.6 | 92.3 |
| Example 6 | antimony-trioxide | 100 | 14.5 | yes | 3.99 | initial stage | 250 | 98.4 | 94.9 | 93.4 |
| | | | | | | 4000 | 254 | 98.3 | 94.8 | 93.2 |
| Comparative Example 1 | antimony-trioxide | 20 | 16.3 | no | 3.42 | initial stage | 284 | 88.4 | 90.1 | 79.7 |
| | | | | | | 4000 | 298 | 85.2 | 88.6 | 75.5 |
| Comparative Example 2 | antimony-trioxide | 200 | 24.2 | yes | 4.00 | initial stage | 254 | 97.7 | 94.0 | 91.8 |
| | | | | | | 4000 | 260 | 97.0 | 92.1 | 89.3 |
| Comparative Example 3 | antimony-trioxide | 200 | 35.6 | no | 4.01 | initial stage | 254 | 97.6 | 93.8 | 91.6 |
| | | | | | | 4000 | 261 | 97.0 | 91.3 | 88.6 |
| Comparative Example 4 | antimonyl-potassium tartarate | — | 45.8 | yes | 4.00 | initial stage | 255 | 97.2 | 93.1 | 90.5 |
| | | | | | | 4000 | 262 | 96.3 | 90.3 | 87.4 |

The invention claimed is:

1. A catalyst for producing acrylic acid, comprising:
a complex oxide containing molybdenum, vanadium, and at least one X component selected from the group consisting of antimony, niobium and tin as the essential components,
wherein:
the complex oxide has a main peak of d=4.00±0.1 angstrom as measured with X-ray diffractometry using Kα ray of Cu,
the X component in the complex oxide after calcination has a particle size not exceeding 20 μm as measured with EPMA analysis, and
the catalyst is prepared by molding a catalyst precursor into a fixed shape and calcining the shaped catalyst precursor to form the complex oxide.

2. A catalyst for producing acrylic acid which is formed by supporting the complex oxide as described in claim 1 on an inert carrier.

3. The catalyst for producing acrylic acid according to claim 1, wherein the complex oxide is represented by the following formula (1):

$$Mo_aV_bX_cA_dB_eC_fD_gO_y \quad (1)$$

wherein Mo is molybdenum; V is vanadium; X is at least one element selected from the group consisting of antimony, niobium and tin; A is at least one element selected from the group consisting of tungsten, nickel, cobalt, tellurium and bismuth; B is at least one element selected from the group consisting of iron, copper, lead and zinc; C is at least one element selected from the group consisting of silicon, titanium and zirconium; D is at least one element selected from the group consisting of alkali metals; and O is oxygen; and a, b, c, d, e, f, g and y are respective atomic ratios of Mo, V, X, A, B, C, D and O; where a=12, 1≦b≦15, 0.01≦c≦10, 0.02≦d≦6, 0.01≦e≦6, 0≦f≦60 and 0≦g≦10; and y is a numerical value determined by the state of oxidation of respective elements.

4. A method for producing acrylic acid by catalytic gas phase oxidation of propane and/or acrolein in the presence of molecular oxygen or a molecular oxygen-containing gas, using a fixed bed shell-and-tube reactor, wherein the reaction is carried out in the presence of a catalyst as described in claim 1.

5. The catalyst for producing acrylic acid according to claim 2, wherein the complex oxide is represented by the following formula (1):

$$Mo_aV_bX_cA_dB_eC_fD_gO_y \quad (1)$$

wherein Mo is molybdenum; V is vanadium; X is at least one element selected from the group consisting of antimony, niobium and tin; A is at least one element selected from the group consisting of tungsten, nickel, cobalt, tellurium and bismuth; B is at least one element selected from the group consisting of iron, copper, lead and zinc; C is at least one element selected from the group consisting of silicon, titanium and zirconium; D is at least one element selected from the group consisting of alkali metals; and O is oxygen; and a, b, c, d, e, f, g and y are respective atomic ratios of Mo, V, X, A, B, C, D and O; where a=12, 1≦b≦15, 0.01≦c≦10, 0.02≦d≦6, $0.01 \leq e \leq 6$, $0 \leq f \leq 60$ and $0 \leq g \leq 10$; and y is a numerical value determined by the state of oxidation of respective elements.

6. A method for producing acrylic acid by catalytic gas phase oxidation of propane and/or acrolein in the presence of molecular oxygen or a molecular oxygen-containing gas, using a fixed bed shell-and-tube reactor, wherein the reaction is carried out in the presence of a catalyst as described in claim 2.

7. A method for producing acrylic acid by catalytic gas phase oxidation of propane and/or acrolein in the presence of molecular oxygen or a molecular oxygen-containing gas, using a fixed bed shell-and-tube reactor, wherein the reaction is carried out in the presence of a catalyst as described in claim 3.

8. A method for producing acrylic acid by catalytic gas phase oxidation of propane and/or acrolein in the presence of molecular oxygen or a molecular oxygen-containing gas, using a fixed bed shell-and-tube reactor, wherein the reaction is carried out in the presence of a catalyst as described in claim 5.

\* \* \* \* \*